(12) United States Patent
Johanson et al.

(10) Patent No.: US 7,074,203 B1
(45) Date of Patent: Jul. 11, 2006

(54) BONE ANCHOR AND DEPLOYMENT DEVICE THEREFOR

(75) Inventors: Mark A. Johanson, Littleton, MA (US); John Rice, Lincoln, MA (US); Rickey Hart, Plainville, MA (US); James Nicholson, Lincoln, MA (US)

(73) Assignee: DePuy Mitek, Inc., Raynham, MA (US)

( * ) Notice: Subject to any disclaimer, the term of this patent is extended or adjusted under 35 U.S.C. 154(b) by 1149 days.

(21) Appl. No.: 09/086,508

(22) Filed: May 28, 1998

Related U.S. Application Data (63) Continuation-in-part of application No. 08/595,772, filed on Feb. 2, 1996, now Pat. No. 5,968,044, which is a continuation-in-part of application No. 08/814,149, filed on Mar. 10, 1997, now Pat. No. 5,911,721, which is a continuation-in-part of application No. 08/163,130, filed on Dec. 6, 1993, now Pat. No. 5,725,529, which is a continuation-in-part of application No. 07/765,445, filed on Sep. 25, 1991, now Pat. No. 5,268,001, which is a continuation-in-part of application No. 07/588,025, filed on Sep. 25, 1990, now abandoned.

(51) Int. Cl.
*A61B 17/56* (2006.01)

(52) U.S. Cl. .............................. 602/72; 411/34; 606/73
(58) Field of Classification Search ............. 606/72–79, 606/104; 411/34, 43
See application file for complete search history.

(56) References Cited

U.S. PATENT DOCUMENTS

| | | | |
|---|---|---|---|
| 204,913 A | 6/1878 | Pratt | |
| 2,267,925 A | 12/1941 | Johnston | 128/92 |
| 2,381,050 A | 8/1945 | Hardinge | |

(Continued)

FOREIGN PATENT DOCUMENTS

| | | |
|---|---|---|
| DE | 3146634 | 11/1981 |
| DE | 3406961 | 9/1985 |
| DE | 85 20206 | 6/1986 |

(Continued)

OTHER PUBLICATIONS

Daniel, et al. "Fixation of Soft Tissue", 1987, The Anterior Cruciate Deficient Knee, New Concepts in Ligament Repair, Ch. 8, pp. 114–125.

Bankhart, "Recurrent Dislocation of Shoulder: The Pathology and Treatment of Recurrent Dislocation of the Shoulder-Joint" 1938, British J. Surgery, vol. 26, pp. 23–29.

(Continued)

*Primary Examiner*—Michael A. Brown
(74) *Attorney, Agent, or Firm*—Nutter, McClennen & Fish LLP (57) ABSTRACT

A rivet-like bone anchor has a floating washer at its head that can adapt to an angled bone surface and, thereby, better secure a tissue thereto. The anchor includes a rivet, an expandable sleeve, and a washer. The rivet includes a head and an elongate body having proximal and distal ends, the head being mounted on the proximal end of the elongate body. The expandable sleeve has an inner bore adapted to receive the rivet body. The washer "floats" at a proximal end of the sleeve. As the rivet is inserted into sleeve, the sleeve expands into an interference fit with the bone. The head of the rivet, moreover, forces the floating washer into contact with the tissue at an angle that conforms to that of the underlying bone surface. A deployment tool permits the anchor to be deployed without application of unnecessary counterforce. The tool includes an outer tube, the distal end of which can hold the anchor housing, e.g., via a screw fit. A rod, which is slidably disposed within the bore of the tube, can be used to push the rivet into the expandable sleeve so that the sleeve expands into the bone, so that the floating washer is forced into position against the bone surface, and so that anchor is broken away from the housing. This can be effected, for example, by squeezing the distal ends of the outer tube and the rod together, e.g., in the manner that the end of a syringe is squeezed.

22 Claims, 7 Drawing Sheets

U.S. PATENT DOCUMENTS

| | | | |
|---|---|---|---|
| 2,551,840 A | 5/1951 | Johansen | 198/192 |
| 3,036,482 A | 5/1962 | Kenworthy et al. | |
| 3,103,926 A | 9/1963 | Cochran et al. | 128/92 |
| 3,406,961 A | 10/1968 | Walton | |
| 3,566,739 A | 3/1971 | Lebar | |
| 3,708,883 A | 1/1973 | Flander | |
| 3,842,824 A | 10/1974 | Neufeld | |
| 4,012,984 A * | 3/1977 | Matuschek | 85/70 |
| 4,013,071 A | 3/1977 | Rosenberg | |
| 4,060,089 A | 11/1977 | Noiles | 128/325 |
| 4,091,806 A | 5/1978 | Aginsky | |
| 4,140,111 A | 2/1979 | Morrill | 606/104 |
| 4,230,544 A | 10/1980 | McRae | |
| 4,299,021 A | 11/1981 | Williams | 29/432 |
| 4,320,544 A | 3/1982 | Bryant et al. | 7/158 |
| 4,408,938 A | 10/1983 | Maguire | |
| 4,415,111 A | 11/1983 | McHarrie et al. | 227/19 |
| 4,438,769 A | 3/1984 | Pratt et al. | 128/334 |
| 4,484,570 A | 11/1984 | Sutter | 606/72 |
| 4,492,226 A | 1/1985 | Belykh et al. | |
| 4,506,670 A | 3/1985 | Crossley | |
| 4,507,817 A | 4/1985 | Staffeld | 7/158 |
| 4,521,147 A * | 6/1985 | King et al. | 411/43 |
| 4,542,539 A | 9/1985 | Row, Jr. et al. | |
| 4,579,491 A * | 4/1986 | Kull | 411/43 |
| 4,590,928 A | 5/1986 | Hunt et al. | |
| 4,597,766 A | 7/1986 | Hilal et al. | |
| 4,627,775 A * | 12/1986 | Dixon | 411/34 |
| 4,632,100 A | 12/1986 | Somers et al. | |
| 4,662,886 A | 5/1987 | Moorse et al. | |
| 4,716,893 A | 1/1988 | Fischer et al. | |
| 4,719,917 A * | 1/1988 | Barrows et al. | 606/220 |
| 4,738,255 A | 4/1988 | Goble et al. | |
| 4,741,330 A | 5/1988 | Hayhurst | |
| 4,774,793 A | 10/1988 | Mayer | |
| 4,778,468 A | 10/1988 | Hunt et al. | |
| 4,828,562 A | 5/1989 | Kenna | |
| 4,834,752 A | 5/1989 | VanKampen | 606/77 |
| 4,858,603 A | 8/1989 | Clemow | 606/77 |
| 4,870,957 A | 10/1989 | Goble | 623/13 |
| 4,871,289 A | 10/1989 | Choiniere | |
| 4,873,976 A | 10/1989 | Schreiber | |
| 4,884,572 A | 12/1989 | Bays et al. | |
| 4,894,063 A | 1/1990 | Nashef | |
| 4,898,156 A | 2/1990 | Gatturna et al. | |
| 4,899,743 A | 2/1990 | Nicholson et al. | |
| 4,919,576 A * | 4/1990 | Louw et al. | 411/34 |
| 4,924,865 A | 5/1990 | Bays et al. | |
| 4,927,421 A | 5/1990 | Goble | 606/73 |
| 4,940,467 A | 7/1990 | Tronzo | |
| 4,944,742 A | 7/1990 | Clemow et al. | |
| 4,976,715 A | 12/1990 | Bays et al. | 606/77 |
| 4,988,351 A | 1/1991 | Paulos et al. | 606/72 |
| 5,013,316 A | 5/1991 | Goble et al. | |
| 5,037,422 A | 8/1991 | Hayhurst et al. | |
| 5,046,513 A | 9/1991 | Gatturna et al. | |
| 5,116,337 A | 5/1992 | Johnson | |
| 5,129,906 A | 7/1992 | Ross et al. | 606/77 |
| 5,141,373 A | 8/1992 | Kendall | |
| 5,141,520 A | 8/1992 | Goble et al. | |
| 5,152,763 A | 10/1992 | Johnson | |
| 5,169,400 A | 12/1992 | Muhling | 606/72 |
| 5,176,682 A | 1/1993 | Chow | |
| 5,203,784 A | 4/1993 | Ross et al. | 606/104 |
| 5,207,679 A | 5/1993 | Li | |
| 5,209,753 A | 5/1993 | Biedermann et al. | |
| RE34,293 E | 6/1993 | Goble et al. | |
| 5,216,914 A | 6/1993 | Homer | |
| 5,224,946 A | 7/1993 | Hyhurst et al. | |
| 5,236,445 A | 8/1993 | Hayhurst et al. | |
| 5,248,231 A | 9/1993 | Denham et al. | |
| 5,257,637 A | 11/1993 | El Gazayerli | |
| 5,258,015 A | 11/1993 | Li et al. | |
| 5,261,914 A | 11/1993 | Warren | 606/73 |
| 5,268,001 A | 12/1993 | Nicholson et al. | 606/72 |
| 5,324,308 A | 6/1994 | Pierce | |
| 5,326,205 A | 7/1994 | Anspach, Jr. et al. | |
| 5,354,298 A | 10/1994 | Lee et al. | |
| 5,380,334 A | 1/1995 | Torrie et al. | 606/104 |
| 5,400,805 A | 3/1995 | Warren | 128/898 |
| 5,411,523 A | 5/1995 | Goble | |
| 5,417,712 A | 5/1995 | Whittaker et al. | |
| 5,423,860 A | 6/1995 | Lizardi et al. | 606/72 |
| 5,458,601 A | 10/1995 | Young, Jr. et al. | |
| 5,464,427 A | 11/1995 | Curtis et al. | |
| 5,472,452 A | 12/1995 | Trott | |
| 5,480,403 A | 1/1996 | Lee et al. | |
| 5,486,197 A | 1/1996 | Le et al. | |
| 5,489,210 A | 2/1996 | Hanosh | |
| 5,496,326 A | 3/1996 | Johnson | |
| 5,501,683 A | 3/1996 | Trott | |
| 5,501,695 A | 3/1996 | Anspach et al. | |
| 5,522,845 A | 6/1996 | Wenstrom, Jr. | |
| 5,540,703 A | 7/1996 | Barker, Jr. et al. | |
| 5,545,180 A | 8/1996 | Le et al. | |
| 5,556,410 A | 9/1996 | Mittermeir et al. | 606/185 |
| 5,571,104 A | 11/1996 | Li | |
| 5,584,835 A | 12/1996 | Greenfield | 606/72 |
| 5,584,836 A | 12/1996 | Ballintyn et al. | 606/73 |
| 5,601,558 A | 2/1997 | Torrie et al. | 606/72 |
| 5,713,903 A * | 2/1998 | Sander et al. | 606/72 |
| 2002/0062151 A1 | 5/2002 | Altman et al. | |

FOREIGN PATENT DOCUMENTS

| | | |
|---|---|---|
| EP | 0 058 744 | 9/1982 |
| EP | 0 124 489 | 11/1984 |
| EP | 0232049 | 8/1987 |
| EP | 0 232 049 | 8/1987 |
| EP | 0 241 240 | 10/1987 |
| EP | 87302940.9 | 10/1987 |
| EP | 0260787 | 3/1988 |
| EP | 0 260 970 | 3/1988 |
| EP | 0 270 704 | 6/1988 |
| EP | 86117360.7 | 6/1988 |
| EP | 0 251 583 | 7/1988 |
| EP | 0 340 159 | 11/1989 |
| EP | 0 409 364 | 1/1991 |
| EP | 90250174.1 | 1/1991 |
| EP | 0557306 | 9/1993 |
| EP | 0 574 707 | 12/1993 |
| EP | 0 611 557 | 8/1994 |
| EP | A-0 611 557 | 8/1994 |
| FR | 2 054 731 | 5/1971 |
| FR | 2 346 591 | 10/1977 |
| FR | 2 622 430 | 5/1989 |
| FR | 2636836 | 3/1990 |
| GB | 2 084 468 | 4/1982 |
| GB | 2 248 778 | 4/1992 |
| WO | WO 88/09157 | 12/1988 |
| WO | WO 89/01767 | 3/1989 |
| WO | WO 91/07929 | 6/1991 |
| WO | WO 92/04874 | 4/1992 |
| WO | WO 92/10149 | 6/1992 |
| WO | WO 95/02998 | 2/1995 |
| WO | WO 95/15726 | 6/1995 |
| WO | WO 95/29636 | 11/1995 |

OTHER PUBLICATIONS

Rowe, et al., "Recurrent Anterior Dislocation of the Shoulder After Surgical Repair", Feb. 1984, J. Bone and Joint Surgery, vol. 66–A, No. 2, pp. 159–168.

Venable, et al., "The Effects of Bone of the Presence of Metals; Based upon Electrolysis", Jan.–Jun. 1937, Annals of Surgery vol. 105, 917–938.

* cited by examiner

BONE ANCHOR AND DEPLOYMENT DEVICE THEREFOR

REFERENCE TO RELATED APPLICATIONS

This application claims the benefit of priority of and is a continuation-in-part of U.S. application Ser. No. 08/595,772, filed on Feb. 2, 1996 now U.S. Pat. No. 5,968,044 and of application Ser. No. 08/814,149, filed on Mar. 10, 1997 now U.S. Pat. No. 5,911,721 and, thereby, of U.S. application Ser. No. 08/163,130 (now U.S. Pat. No. 5,725,529) filed on Dec. 6, 1993 and, thereby, of U.S. application Ser. No. 07/765,445 (now U.S. Pat. No. 5,268,001) filed on Sep. 25, 1991 and, thereby, of U.S. application Ser. No. 07/588,025 (now abandoned) filed on Sep. 25, 1990.

BACKGROUND OF THE INVENTION

The present invention is directed to a bone anchor for attaching tissue to bone, and to a device for deploying such an anchor in bone. More specifically, the invention is directed to a bone anchor which employs a "floating" washer that conforms to the angle of the bone surface to hold tissue in place, and to a deployment device having a plunger-like configuration that facilitates deployment of such an anchor.

Soft tissue, such as tendon, may become detached from a patient's bone as a result of injury or a medical procedure. In either case, the tissue must be re-attached in order to permit healing. Medical devices used to perform this function are known as bone anchors.

Traditionally, bone anchors were merely tacks or nails that were hammered through a patient's soft tissue and directly into the patient's bone. Anchors of this type, however, had many deficiencies. For example, they were prone to coming out of the bone, particularly in cases where patients were relatively active. In addition, because the anchors were hammered directly into the bone, deployment was difficult and could sometimes result in hairline fractures.

In recent times, more sophisticated bone anchors have been developed which alleviate some of the problems mentioned above. For example, many bone anchors now include prongs or something similar, which reduce the chances that the anchor will dislodge from the bone. Likewise, bone anchors have now been developed which can be inserted into pre-formed holes in bone, rather than being hammered.

When affixing tissue directly to bone, it is often desirable to deploy the bone anchor at an angle that is normal to the bone surface. If this is not done, then sufficient contact may not be achieved with the surrounding tissue to hold the tissue in place. Understandably, achieving such placement can be difficult when the anchors are placed endoscopically.

In addition to the foregoing, the force required to deploy a conventional bone anchor often makes deployment problematic. Driving a tack or nail-like anchor into bone, for example, is difficult if the surgeon does not have adequate leverage on the bone to counterbalance the force of impact.

Thus, there exists a need for a bone anchor which does not need to be deployed at a precise angle in order to attach tissue to bone reliably, and a device for deploying such an anchor which does not require a surgeon to impart substantial counterforce against the device during bone anchor deployment.

In view of the foregoing, an object of the invention is to provide improved bone anchors and methods for deployment thereof. A related object is to provide improved devices for deploying such anchors.

A further object is to provide anchors that attach tissue firmly and reliably, regardless of the angle of deployment.

A still further object is to provide anchors, methods and devices for deployment thereof suitable for use in endoscopic procedures.

Yet a still further object is to provide such anchors, methods and devices that can be deployed easily and without application of unnecessary leverage or counterforces.

SUMMARY OF THE INVENTION

The present invention addresses the foregoing objects by providing a rivet-like bone anchor having a floating washer at its head that can adapt to an angled bone surface and, thereby, better secure a tissue thereto. The invention also provides a deployment tool that permits the anchor to be deployed without application of unnecessary counterforce.

Thus, according to one aspect, the present invention is a bone anchor which includes a rivet, an expandable sleeve, and a washer. The rivet includes a head and an elongate body having proximal and distal ends, the head being mounted on the proximal end of the elongate body. The expandable sleeve has an inner bore adapted to receive the rivet body. The washer "floats" at a proximal end of the sleeve. As the rivet is inserted into sleeve, the sleeve expands into an interference fit with the bone. The head of the rivet, moreover, forces the floating washer into contact with the tissue at an angle that conforms to that of the underlying bone surface.

In other aspects of the invention, an external surface of the expandable sleeve and/or the rivet has one or more annular ribs, threads or protrusions. These increase the strength of the interference fits between the rivet and the sleeve, as well as between the sleeve and the bone, thereby reducing the chances that the anchor will dislodge. The washer can likewise include ridges, teeth or other protrusions that enhance fixation of the tissue upon deployment.

In still other aspects of the invention, the bone anchor includes a housing which is frangibly coupled to the expandable sleeve via breakable flanges. The housing, which can be used to affix the anchor to the delivery device, can also protect and store the rivet prior to deployment. During deployment, the head of the rivet breaks the flanges of the housing, thereby freeing the housing from the anchor.

According to another aspect, the present invention provides an apparatus for deploying a bone anchor of the type described above. The apparatus includes an outer tube, the distal end of which can hold the anchor housing, e.g., via a screw fit. A rod, which is slidably disposed within the bore of the tube, can be used to push the rivet into the expandable sleeve so that the sleeve expands into the bone, so that the floating washer is forced into position against the bone surface, and so that anchor is broken away from the housing. This can be effected, for example, by squeezing the proximal ends of the outer tube and the rod together, e.g., in the manner that the end of a syringe is squeezed.

By virtue of this design, the counterforce which a surgeon must impart to the apparatus during bone anchor deployment is eliminated. More specifically, because the outer tube is coupled to the expandable sleeve and because the rod pushes on the rivet, there are no net forces that must be counterbalanced during at least the initial stage of deployment.

According to another aspect, the present invention is a method of deploying a bone anchor of the type described above using a deployment device of the type described above. The method includes pulling the tissue into position over the bone with a guide wire, e.g., a pin or K-wire, and drilling a hole in the bone, e.g., with a drill bit fitted over the end of the guide wire. With the guide wire holding the tissue in place over the bone hole, the bone anchor is then threaded down the wire and into position for deployment (e.g., with the sleeve in the bone hole and the floating washer resting against the tissue and bone surface). The deployment device, which is preferably threaded to the anchor, is simultaneously slid into position for deployment.

According to yet another aspect of the invention, the tissue is pierced and pulled into position over a predrilled bone hole via a guide or probe integral to, and extending from, the distal end of the outer tube. With the guide or probe holding the tissue in place over the bone hole, the bone anchor is passed through the outer tube, threaded through the tissue and into the bone hole.

Still further aspects of the invention provide for securing the sleeve into the bone hole by threading it through clockwise (or counter-clockwise) rotation of the outer tube.

The rivet is deployed by squeezing the proximal end of the outer tube and inner rod together in a syringe-like motion, or put another way, by applying downward force to the inner rod and upward force to the outer tube thereby forcing the rivet out of the housing and into the expandable sleeve. Continued application of these forces, at least partially sets the floating washer in conformity to the angle of the underlying bone surface and causes the frangible flanges to break, thereby freeing the housing from the sleeve. Once the anchor is at least partially deployed, the deployment device and attached housing (sans anchor) are removed from the site. The inner tube of the deployment device is then rethreaded down the K-wire so that its distal end re-abuts the head of the rivet. By applying force (e.g., tapping) to the proximal end of the inner rod, the rivet is fully set, fully fixing the washer at the angle of the underlying bone surface.

A more complete understanding of the invention can be obtained by reference to the following detailed description of the preferred embodiments thereof in connection with the attached drawings.

BRIEF DESCRIPTION OF THE DRAWINGS

A more complete understanding of the invention may be attained by reference to the drawings, in which.

DETAILED DESCRIPTION OF THE PREFERRED EMBODIMENTS

Figure 1:
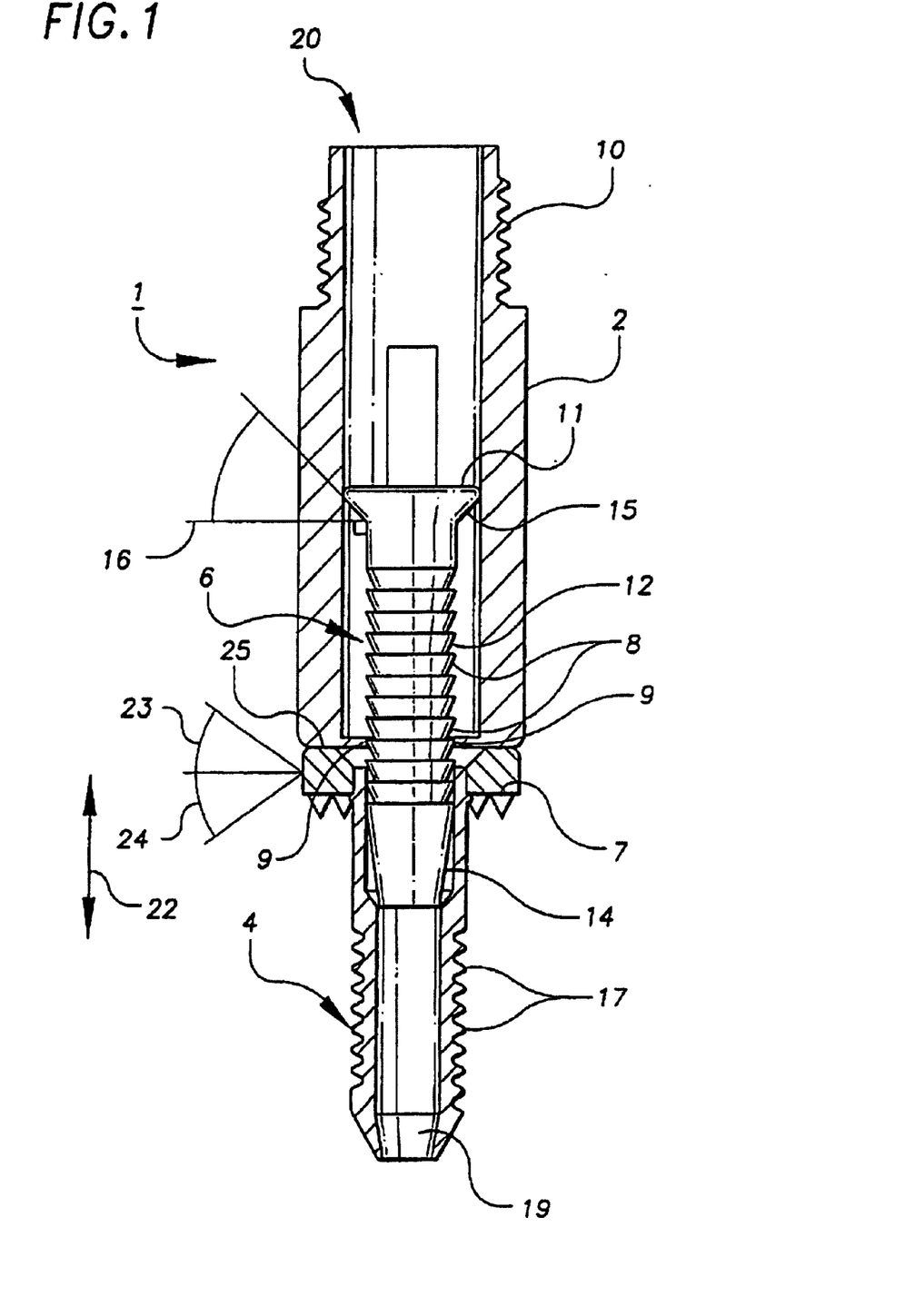
FIG. 1 is a close-up view of a bone anchor in accordance with the present invention, in which the bone anchor's rivet is not deployed.
Figure 2:
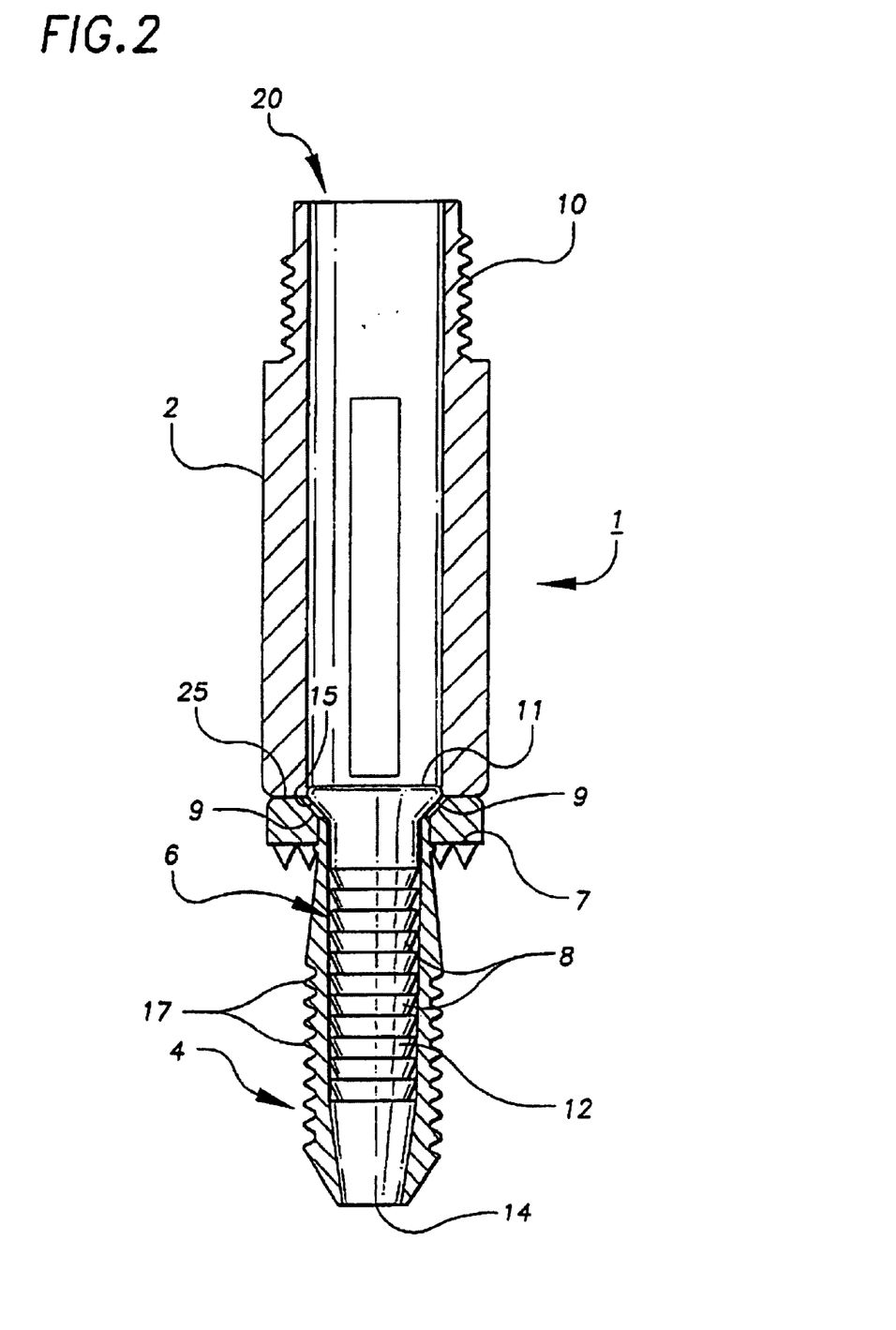
FIG. 2 is a close-up view of a bone anchor in accordance with the present invention, in which the bone anchor's rivet is deployed.

FIGS. 1 and 2 are close-up, cut-away views of a bone anchor according to the present invention. As shown in FIG. 1, bone anchor 1 includes housing 2, expandable 5 sleeve 4, rivet 6, floating washer 7, breakable flanges 9, and threading 10. In preferred embodiments of the invention, some or all of these components are made of a bioabsorbable material which dissolves in a patient's body over a period of time leaving little or no trace. Alternatively, bone anchor 1 may be made of other biocompatible materials, such as conventional plastics or the like.

Rivet 6 is comprised of head 11, elongate body 12, tapered tip 14, and a centerbore (not shown) running therethrough. Head 11 is located at the proximal end of rivet 6 and has a diameter which is greater than that of either elongate body 12 or tapered tip 14. Head 11 also includes undersurface 15. Undersurface 15 can be formed with a spherical radius or, alternatively, angled relative to a longitudinal axis of the elongate body. Thus, as shown in the illustration, the undersurface is angled relative to plane 16 which, as shown in FIG. 1, bisects elongate body 12 at a right angle. Preferably, undersurface 15 is angled at 45 degrees; although other angles may be used. Elongate body 12 includes annular ribs 8 on an outer surface thereof, which are adapted to aid in maintaining rivet 6 in sleeve 4. It should be noted, however, that elongate body 12 need not include annular ribs in order to perform its function. Tapered tip 14 is located at the distal end of rivet 6, and has a diameter which decreases gradually from the diameter of elongate body 12 to less than that of inner bore 19 of expandable sleeve 4.

Prior to deployment of bone anchor 1, rivet 6 is housed in housing 2, as shown in FIG. 1. Housing 2 is preferably cylindrical in shape and includes threading 10 at first open end 20. Threading 10 is adapted to connect bone anchor 1 to a bone anchor delivery device, such as that described in detail below. Housing 2 is integrally coupled with expandable sleeve 4 via flanges 9, which are sized to break in response to either downward or upward pressure against head 11 so as to disconnect (i.e., free) housing 2 from expandable sleeve 4.

Expandable sleeve 4 includes inner bore 19, as noted above, and is fabricated of a material which is capable of expanding into an interference fit with a bone hole. Inner bore 19 has a diameter that is less than the diameter of elongate body 12, but which is greater than or equal to a diameter of tapered tip 14. As a result of these dimensions, expandable sleeve 4 is able to receive rivet 6, distal-end-first. As described in more detail below, expandable sleeve 4 expands as elongate body 12 moves into expandable sleeve 4, eventually resulting in the arrangement shown in FIG. 2, in which expandable sleeve 4 is fully expanded. When bone anchor 1 is deployed in a hole in a bone, this expansion results in an interference fit between expandable sleeve 4 and the bone. To aid in expansion, expandable sleeve 4 also may include radial or longitudinal slots (not shown) which runs all or part-way along expandable sleeve 4. In addition, a membrane may also be included on the slot, which permits expansion while, at the same time, guarding against breakage of expandable sleeve 4.

The outer surface of expandable sleeve 4 includes annular ribs or threads 17 along at least a portion thereof. Annular ribs or threads 17 contact sides of a bone hole into which bone anchor 1 is implanted and, when expandable sleeve 4 is expanded, assist in maintaining bone anchor 1 in the bone. This feature of the invention is described in more detail below.

Disposed around the outer surface of expandable sleeve 4 is washer 7. Washer 7 may be of any shape, i.e., it may be elliptical, circular, etc., and may include ridges or other protrusions on its undersurface for improved contact with tissue or bone. When bone anchor 1 is not deployed in a bone, washer 7 "floats", meaning that it is capable of at least longitudinal motion and limited angular motion relative to expandable sleeve 4. Washer 7 may be capable of lateral motion relative to expandable sleeve 4 as well. Thus, referring to FIG. 1, washer 7 is capable of longitudinal motion along line 22 and of angular motion at, e.g., angles 23 and 24. This longitudinal motion and angular rotation is possible when expandable sleeve 4 is fully unexpanded and, preferably, also when it is fully expanded. Washer 7 also has a top surface 25 which abuts with undersurface 15 of rivet 6, and which may or may not be angled or radiused relative thereto. In the embodiment shown in FIGS. 1 and 2, top surface 25 of washer 7 is not angled or radiused.

Figure 3:
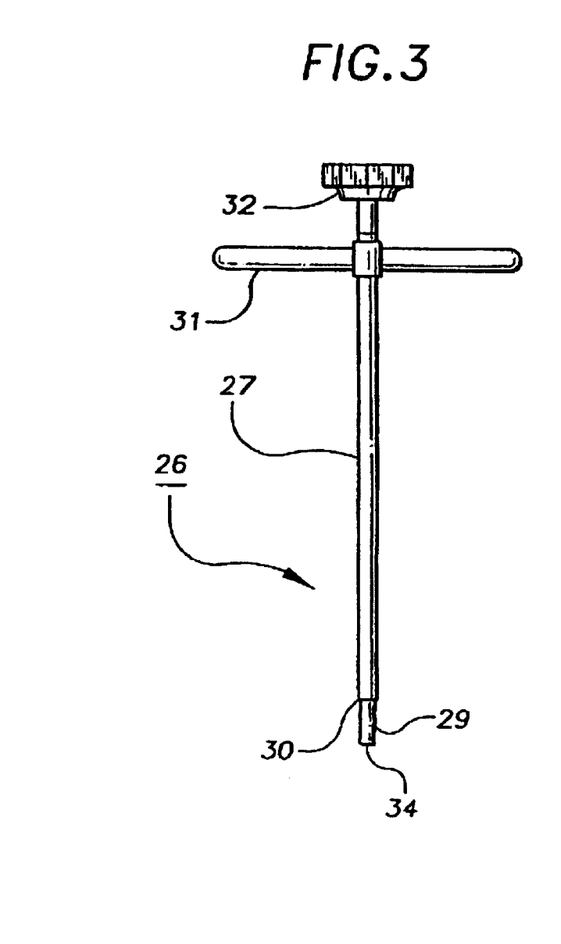
FIG. 3 shows a bone anchor deployment device in accordance with the present invention.
Figure 4:
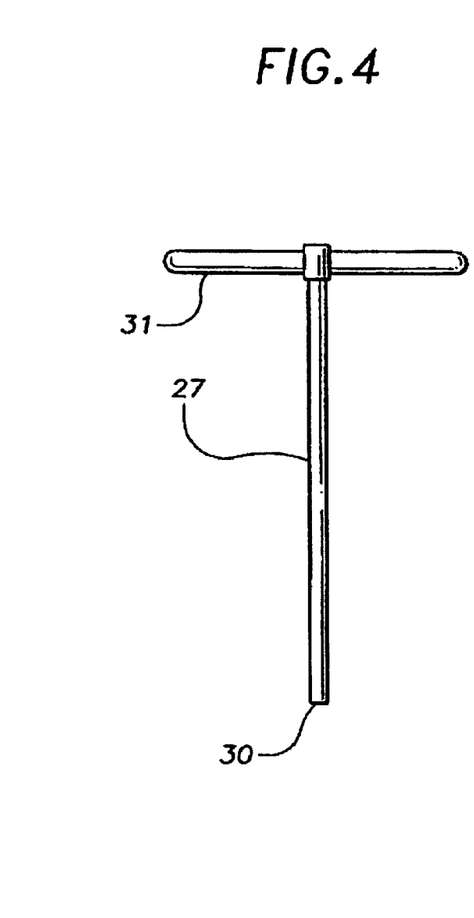
FIG. 4 shows an outer tube of the bone anchor deployment device shown in FIG. 3.

Bone anchor 1 is deployed into a hole in a bone using a plunger-like deployment device, such as that shown in FIG. 3. As shown in FIG. 3, bone anchor deployment device 26 is comprised of tube 27 and rod 29. These components may be fabricated of any material; although stainless steel is used in the preferred embodiment. Tube 27, which is shown in FIG. 4, has a bore (not shown) therethrough for receiving rod 29. At distal end 30, the inner surface of tube 27 includes threading (not shown). This threading is adapted to mate with threading of a bone anchor, such as bone anchor 1, in order to hold the housing of the bone anchor substantially immobile during deployment. Tube 27 also includes "T"-shaped handle 31 at its proximal end. Handle 31 interacts with knob 32 of rod 29 so as to limit the motion of rod 29 relative to tube 27.

Figure 5:
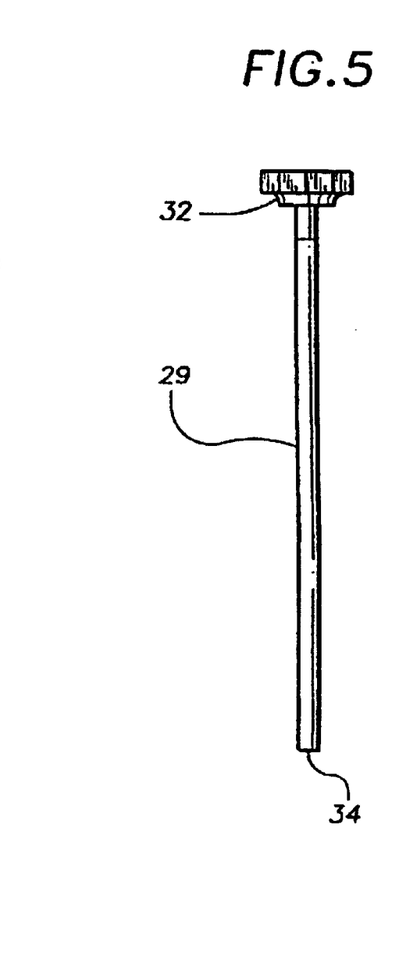
FIG. 5 shows an inner rod of the bone anchor deployment device shown in FIG. 3.

In this regard, rod 29, which is shown in FIG. 5, is removably disposed within the bore of tube 27 and is slidable therein. That is, rod 29 can be removed from tube 27 merely by sliding rod 29 out of tube 27. In addition, rod 29 is capable of sliding within tube 27 such that distal end 34 of rod 29 extends out from tube 27 (see FIG. 3). This feature of rod 29 makes it possible for rod 29 to move within at least a portion of the housing of a bone anchor connected to tube 27, as described in more detail below. As noted above, rod 29 also includes knob 32, which contacts handle 31 of tube 27 in order to limit the motion of distal end 34 relative to tube 27. Finally, rod 29 includes a centerbore (not shown) which is capable of receiving a guide wire, such as a K-wire and/or the like.

Figure 6:
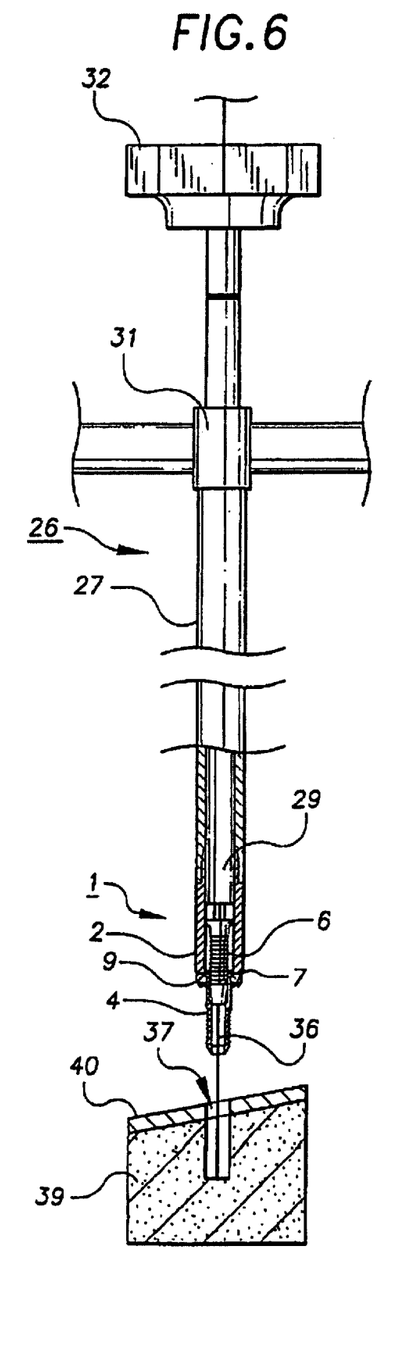
FIGS. 6 through 12 show a process for deploying the bone anchor shown in FIG. 1 into a bone using the bone anchor deployment device shown in FIG. 3.

FIGS. 6 through 12 explain operation of both bone anchor 1 and deployment device 26 in the context of deploying a bone anchor into a bone during an endoscopic or other surgical procedure. To initiate such a procedure, a K-wire is inserted through the tissue (e.g., tendon) and into the bone at which a bone anchor is to be deployed. A hole is then formed in the bone at that location, e.g., via a drill bit or other cutting device disposed at the distal end of the K-wire. In this regard, hole 37 can be formed by any conventional means. In preferred embodiments of the invention, however, a drill bit or other cutting device (not shown) is slid over K-wire 36 so as to secure the drill bit to K-wire 36 in order to drill hole 37. Thereafter, the drill is removed from K-wire 36. In these embodiments of the invention, a drill guide which is used with such a drill may take the place of the K-wire entirely. The following, however, assumes that a K-wire is used. The result of these steps is shown in FIG. 6, namely K-wire 36 in hole 37.

After, before or during formation of hole 37 in bone 39, a bone anchor, such as that shown in FIG. 1, is installed in a bone anchor deployment device, such as that shown in FIG. 3. Specifically, with reference to FIG. 6, housing 2 of bone anchor 1 is screwed into inner threads of tube 27 on deployment device 26. Once this has been done, bone anchor deployment device 26 and bone anchor 1 are slid over K-wire 36 via respective throughbores of sleeve 4, rivet 6 and rod 29. This is shown in FIG. 6.

Figure 7:
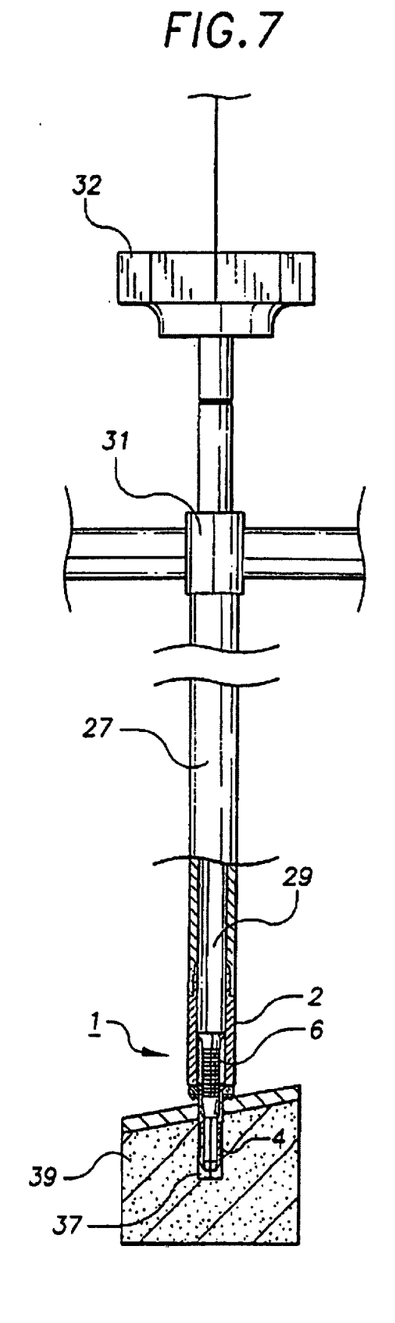

Next, as shown in FIG. 7, expandable sleeve 4 on bone anchor 1 is inserted through soft tissue 40 and into hole 37 of bone 39. Since expandable sleeve 4 is not expanded at this stage of the deployment process, little actual pressure is required on the part of the surgeon in order to insert expandable sleeve 4 into hole 37. As shown in FIG. 7, rod 29 may also be moved into contact with rivet 6 at this point by pressing down on knob 32. This pressure may be applied by any means, such as by a surgeon "squeezing" handle 31 and knob 32 together using one hand in a syringe-like manner. Alternatively, hammer blows may be applied to knob 32 while holding tube 27 in place.

In any event, following insertion of expandable sleeve 4 into hole 37, additional pressure is applied to knob 32 to begin initial deployment of rivet 6 into expandable sleeve 4. Specifically, downward pressure is applied to rivet 6 by sliding rod 29 downwards relative to tube 27 so as to force rod 29 into housing 2 and to force rivet 6 out of housing 2 and into expandable sleeve 4. Since housing 2 is held substantially immobile by tube 27, and since housing 2 is connected to sleeve 4, the process of deploying rivet 6 has little or no effect on the bone. That is, the downward force applied to rivet 6 is not significantly imparted to bone 39 because rivet 6 moves within housing 2 and sleeve 4, both of which are held in place by tube 27. As a result, bone 39 moves little during initial deployment of rivet 6.

Figure 8:
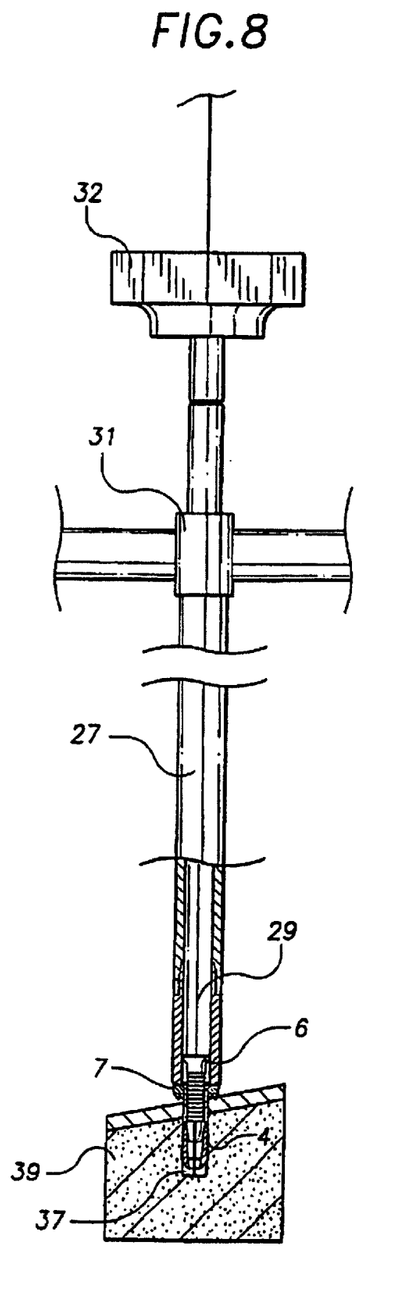
Figure 9:
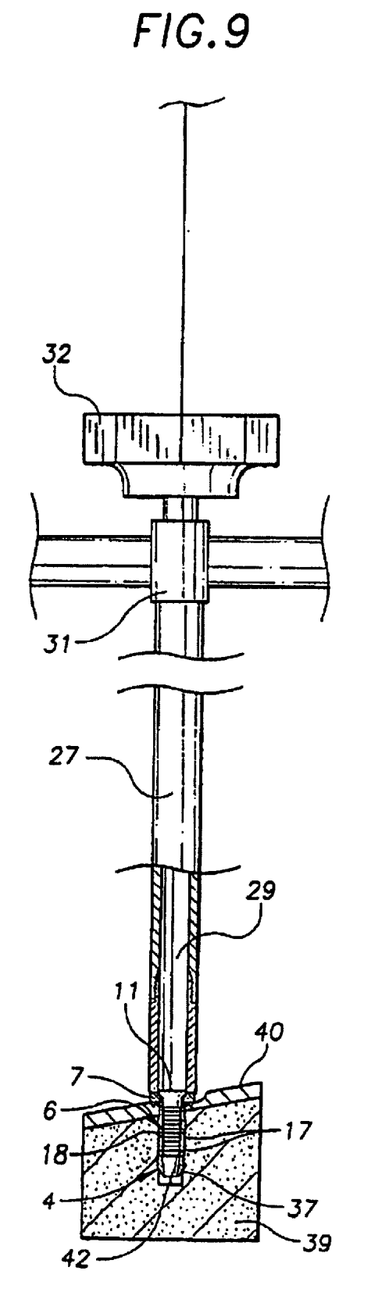

As shown in FIGS. 8 and 9, as rivet 6 is deployed into expandable sleeve 4, expandable sleeve 4 expands within hole 37. This expansion results in an interference fit between bone anchor 1 (meaning rivet 6 and expandable sleeve 4) and bone 39. Annular ribs 17 on expandable sleeve 4 strengthen this interference fit by coming into relatively tight contact with the sides of hole 37. In addition, annular ribs 18 on rivet 6 also enhance the reliability of the interference fit by reducing the chances that rivet 6 will come out of expandable sleeve 4.

The initial deployment process depicted in FIGS. 6 through 9 causes rivet 6 to be moved substantially, but not completely, into hole 37 of bone 39. That is, as shown in FIG. 9, following initial deployment, there is still a space 42 between rivet 6 and a bottom of hole 37. Moreover, as also shown in FIG. 9, following initial deployment, washer 7 is not firmly sandwiched between head 11 of rivet 6 and tissue 40 on bone 39. Since washer 7 is preferably firmly sandwiched between head 11 and tissue 40 in order for bone anchor 1 to function property, additional steps are performed in order to complete deployment.

Specifically, in order to complete deployment of bone anchor 1, deployment device 26 must be removed from K-wire 36 and housing 2 must be disconnected from expandable sleeve 4. One advantage of the present invention is that these actions may be performed concurrently. More specifically, as noted above, bone anchor 1 includes flanges 9 which break when sufficient force is applied thereto. In the present invention, this force may comprise either contact with head 11 during downward movement of rivet 6 into expandable sleeve 4, or contact with head 11 during upward movement of tube 27. In this regard, to break flanges 9 during upward movement of tube 27, downward pressure is retained on rod 29 and upward pressure is applied to tube 27.

Figure 10:
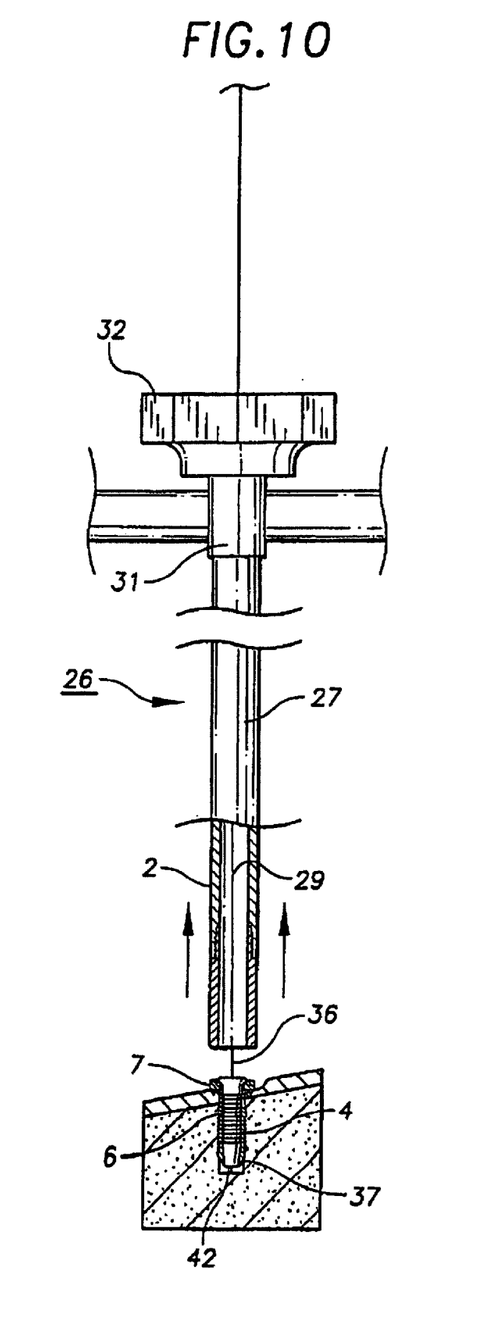
Figure 11:
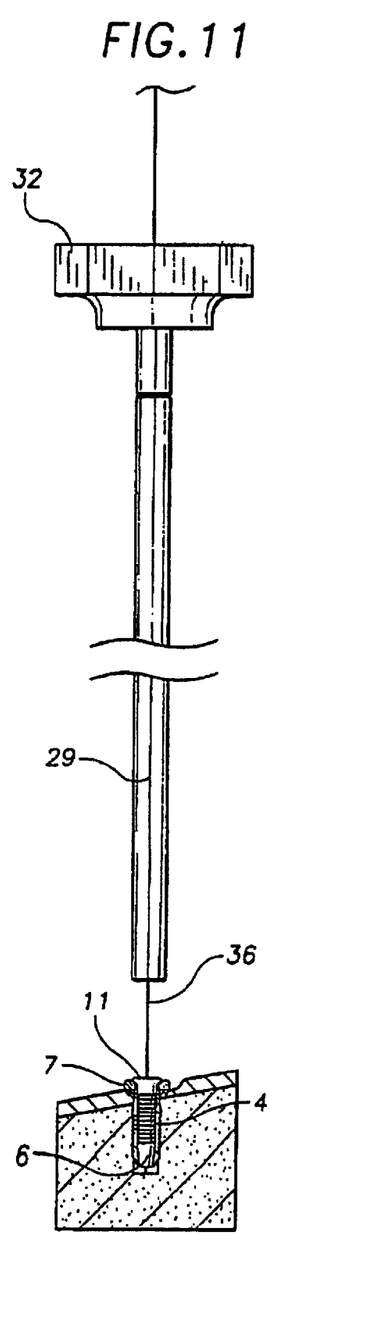
Figure 12:
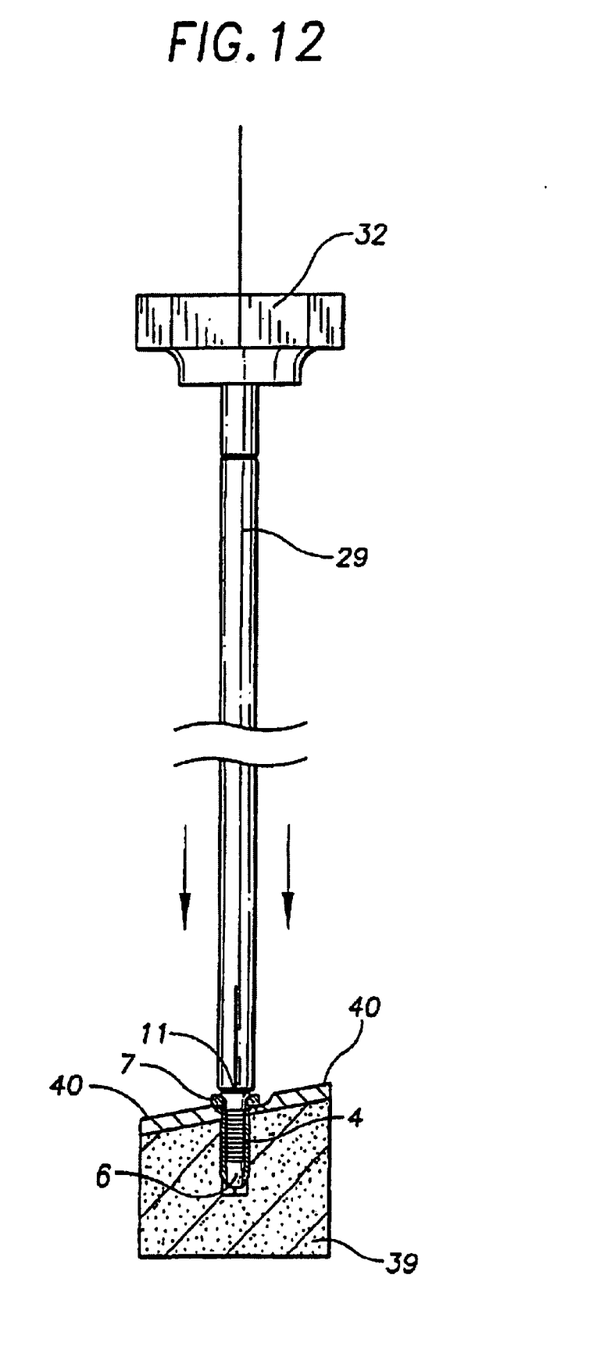

In any event, as shown in FIG. 10, once flanges 9 break, deployment device 26, with housing 2 still attached thereto, can be slid off of K-wire 36, leaving rivet 6, washer 7, and expandable sleeve 4 within bone 39. Final deployment then can begin by disconnecting rod 29 from tube 27 (i.e., by sliding rod 29 out of tube 27) and sliding rod 29 back over K-wire 36, as shown in FIG. 11. Washer 7 is then set in place by applying a force to knob 32 of rod 29 by way of hammer blows or the like. Because this additional force can be applied via hammer blows or the like, the need for a surgeon to exert counterforce during final deployment is reduced.

The additional force applied above causes rivet 6 to move substantially all the way into hole 37, thereby resulting in firm contact between head 11 and washer 7. As a result of this contact, head 11 forces washer 7 against tissue 40 so that washer 7 is firmly sandwiched between head 11 and tissue 40. In this regard, since washer 7 floats relative to bone surface, head 11 forces washer 7 against tissue 40 so that washer 7 is substantially parallel to a surface of bone 39, i.e., so that washer 7 is disposed at an angle that substantially conforms to a surface of the underlying bone (see FIG. 12). The angle or radii of the undersurface of head 11 described above facilitates this placement. As a result, washer 7 is able to hold tissue 40 in place. Thus, by using a floating washer in this manner, the invention reduces the need to implant the bone anchor at a precise angle relative to the bone.

The present invention has been described with respect to particular illustrative embodiments. It is to be understood that the invention is not limited to the above-described embodiments and modifications thereto, and that various changes and modifications may be made by those of ordinary skill in the art without departing from the spirit and scope of the appended claims.

We claim:

1. A bone anchor comprising:
   a rivet which includes a head and an elongate body having proximal and distal ends, the head being mounted on the proximal end of the elongate body;
   an expandable sleeve having an inner bore adapted to receive the elongate body of the rivet; and
   a washer which floats and is disposed about of the expandable sleeve;
   wherein, as the rivet is received in the expandable sleeve, the sleeve expands in an interference fit with surrounding bone and the head of the rivet forces the washer into contact with tissue adjacent to the bone, the washer being forced into contact with the tissue at an angle that conforms to an angle of a surface of the bone.

2. A bone anchor according to claim 1, wherein an external surface of the expandable sleeve includes one or more protrusions.

3. A bone anchor according to claim 1, wherein the rivet includes a centerbore which is capable of receiving any of a guide wire, guide pin and K-wire.

4. A bone anchor according to claim 1, further comprising:
   a housing which is frangibly coupled to the expandable sleeve via breakable flanges, the housing being adapted to store the rivet prior to insertion of the rivet into the expandable sleeve, and being adapted to affix the bone anchor to a delivery device;
   wherein, during deployment of the bone anchor, the head of the rivet breaks the flanges of the housing, thereby freeing the housing from the bone anchor.

5. A bone anchor for attaching tissue to bone, the bone anchor comprising:
   a rivet having an elongate body and a head disposed on a proximal end thereof;
   an expandable sleeve for insertion into an opening in a bone, the expandable sleeve having an inner bore adapted to receive at least a portion of the elongate body of the rivet; and
   a floating washer that is disposed about the expandable sleeve and that floats relative thereto;
   wherein motion of the portion of the elongate body of the rivet within the inner bore of the expandable sleeve from a proximal end to a distal end thereof causes (i) the expandable sleeve to expand into an interference fit with the bone, and (ii) secures the floating washer relative to the bone.

6. A bone anchor according to claim 5, wherein the floating washer is secured to the bone at an angle that substantially corresponds to a surface of the bone.

7. A bone anchor for attaching tissue to a bone, the bone anchor comprising:
   a rivet which includes a head and an elongate body having proximal and distal ends, the head being mounted on the proximal end of the elongate body;
   an expandable sleeve which is adapted to move between an unexpanded state and an expanded state, the expandable sleeve having an inner bore which is adapted to receive the elongate body of the rivet distal-end-first so as to cause the expandable sleeve to go from the unexpanded state to the expanded state; and
   a washer which surrounds the expandable sleeve and which is capable of both longitudinal motion and of limited angular rotation relative to the head of the rivet, wherein the head of the rivet is adapted to sandwich the washer between the tissue and the head of the rivet when the bone anchor is deployed in the bone so as to hold the tissue substantially in place relative to the bone.

8. A bone anchor according to claim 7, wherein the elongate body has a first diameter and, when the expandable sleeve is in an unexpanded state, the inner bore of the expandable sleeve has a second diameter which is less than the first diameter; and
   wherein the distal end of the elongate body comprises a tapered tip, the tapered tip having a diameter which gradually decreases to less than the second diameter of the inner bore.

9. A bone anchor according to claim 7, wherein an external surface of the expandable sleeve includes one or more protrusions.

10. A bone anchor according to claim 7, wherein the rivet includes a centerbore which is capable of receiving any of a guide wire, guide pin and K-wire.

11. A bone anchor according to claim 7, further comprising a housing which is removably connected to the expandable sleeve via breakable flanges, the housing being adapted to store the rivet prior to insertion of the rivet into the expandable sleeve;
   wherein the head of the rivet is adapted to contact the breakable flanges during deployment of the bone anchor so as to break the breakable flanges, thereby disconnecting the housing from the expandable sleeve and leaving the bone anchor in the bone.

12. A bone anchor according to claim 11, wherein the housing has a substantially cylindrical shape and mates to a deployment device used to deploy the bone anchor in bone.

13. A bone anchor according to claim 7, wherein the head of the rivet has an undersurface for contacting the washer, the rivet having an undersurface that is any of radiused or angled relative to an axis of the elongate body.

14. A bone anchor according to claim 7, wherein the washer has a top surface which interacts with the head of the rivet and which is any of radiused or angled relative to an undersurface of the head of the rivet.

15. A bone anchor according to claim 7, wherein, when the bone anchor is deployed in the bone, the rivet holds the washer at an angle relative to the head of the rivet such that the washer is substantially parallel to a surface of the bone.

16. A bone anchor according to claim 7, wherein at least one of the rivet, the washer, and the sleeve are bioabsorbable.

17. A bone anchor according to claim 7, wherein the rivet includes one or more annular ribs.

18. A bone anchor according to claim 7, wherein the sleeve may include one or more slots which runs at least part way along the sleeve.

19. A method of deploying a bone anchor into a bone using a bone anchor deployment device, where (i) the bone anchor has a housing which stores a rivet and a sleeve which receives the rivet from the housing, the sleeve being connected to the housing by breakable flanges, (ii) the bone anchor deployment device has a tube which holds the housing in place and a rod within the tube which is movable relative to the tube and within the housing held by the tube, and (iii) the rivet, the sleeve, and the rod each have a throughbore, the method comprising the steps of:

positioning a distal end of a K-wire at a location in bone where the anchor is to be deployed;

drilling a hole in the bone at that location;

inserting the sleeve into the hole in the bone by sliding the bone anchor and the bone anchor deployment device over the K-wire via respective throughbores of the sleeve, the rivet, and the rod;

deploying the rivet in the sleeve by applying downward pressure to the rod relative to the tube so as to force the rod into the housing held by the tube, thereby forcing the rivet out of the housing; and removing the housing from the sleeve while leaving the sleeve and the rivet in the hole in the bone, the removing step removing the housing by retaining a force on the rod and applying a counterforce to the tube so as to cause the breakable flanges to break, thereby disconnecting the housing from the sleeve.

20. A method according to claim 19, further comprising the steps of:

removing the deployment device, including the housing of the bone anchor, from the guide wire, guide pin and K-wire disconnecting the rod from the tube;

sliding the rod back over the K-wire so that the rod is in contact with the head of the rivet; and applying force to the rod so as to move the rivet still further into the sleeve.

21. A method according to claim 20, wherein the rod includes a knob and the pressure is applied to the rod by hammering the knob of the rod.

22. A method according to claim 20, wherein the bone anchor further comprises a washer which is disposed around the sleeve and which is capable of both longitudinal motion and limited angular rotation relative to the sleeve; and wherein forcing the rivet still further into the sleeve causes the rivet to set the washer at an angle relative to the head of the rivet such that the washer is substantially parallel to a surface of the bone.

* * * * *